US012788956B2

(12) United States Patent
Solosko

(10) Patent No.: US 12,788,956 B2
(45) Date of Patent: Nov. 10, 2026

(54) VASCULAR ACCESS DEVICE WITH EXTENDABLE CATHETER

(71) Applicant: Becton, Dickinson and Company, Franklin Lakes, NJ (US)

(72) Inventor: Thomas A Solosko, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 641 days.

(21) Appl. No.: 18/199,068

(22) Filed: May 18, 2023

(65) Prior Publication Data

US 2023/0372689 A1 Nov. 23, 2023

Related U.S. Application Data

(60) Provisional application No. 63/343,743, filed on May 19, 2022.

(51) Int. Cl.
*A61M 39/02* (2006.01)
*A61M 25/06* (2006.01)

(52) U.S. Cl.
CPC ...... *A61M 39/0247* (2013.01); *A61M 25/065* (2013.01); *A61M 2039/0258* (2013.01)

(58) Field of Classification Search
CPC ...... A61M 39/0247; A61M 2039/0258; A61M 2005/14252; A61M 2005/1585; A61M 25/0606; A61M 2025/0175; A61B 5/153
See application file for complete search history.

(56) References Cited

U.S. PATENT DOCUMENTS

| | | | | |
|---|---|---|---|---|
| 5,338,314 A | | 8/1994 | Ryan | |
| 6,699,221 B2 | * | 3/2004 | Vaillancourt ......... | A61M 39/26 604/167.03 |
| 8,491,568 B2 | * | 7/2013 | Schertiger ............. | F16L 19/083 604/535 |
| 9,399,120 B2 | | 7/2016 | Burkholz | |
| 10,265,466 B2 | * | 4/2019 | Cole ..................... | A61M 5/172 |
| 2014/0039399 A1 | | 2/2014 | Burkholz | |
| 2020/0078579 A1 | | 3/2020 | Harding et al. | |
| 2020/0121284 A1 | | 4/2020 | Schaer et al. | |
| 2020/0155809 A1 | | 5/2020 | Burkholz et al. | |
| 2020/0316359 A1 | | 10/2020 | Tagge et al. | |
| 2020/0330726 A1 | | 10/2020 | Bornhoft et al. | |
| 2022/0023592 A1 | | 1/2022 | Scherich et al. | |

FOREIGN PATENT DOCUMENTS

| | | |
|---|---|---|
| EP | 2895230 B1 | 7/2018 |
| WO | WO2010141563 A2 | 12/2010 |
| WO | WO2015164653 A1 | 10/2015 |
| WO | WO2018182836 A1 | 10/2018 |
| WO | WO2020033141 A1 | 2/2020 |

* cited by examiner

*Primary Examiner* — Laura A Bouchelle
(74) *Attorney, Agent, or Firm* — The Webb Law Firm

(57) ABSTRACT

A vascular access device includes an adapter body having a first end and a second end positioned opposite the first end, with the adapter body defining a passageway, a catheter received by the adapter body, a needle received by the adapter body with a portion of the needle positioned within the catheter, and a seal assembly including a seal body positioned within the passageway of the adapter body and an actuator. The seal body forms a seal with the adapter body and the catheter is connected to the seal body. The actuator is configured to move the seal body from a first position within the adapter body to a second position within the adapter body that is spaced from the first position.

15 Claims, 12 Drawing Sheets

VASCULAR ACCESS DEVICE WITH EXTENDABLE CATHETER

CROSS-REFERENCE TO RELATED APPLICATION

The present application claims priority to U.S. Provisional Application Ser. No. 63/343,743 entitled "Vascular Access Device with Extendable Catheter" filed May 19, 2022, the entire disclosure of which is hereby incorporated by reference in its entirety.

BACKGROUND OF THE INVENTION

Field of the Invention

The present disclosure relates to a vascular access device with an extendable catheter.

Description of Related Art

Catheters are frequently utilized to administer fluids into and out of the body. Patients in a variety of settings, including in hospitals and in home care, receive fluids, pharmaceuticals, and blood products via a vascular access device inserted into a patient's vascular system. Catheters of various types and sizes have been used extensively in a variety of procedures including, but not limited to, treating an infection, providing anesthesia or analgesia, providing nutritional support, treating cancerous growths, maintaining blood pressure and heart rhythm, and many other clinical uses. A common vascular access device is a plastic catheter that is inserted into a patient's vein. The catheter length may vary from a few centimeters for peripheral access to many centimeters for central access. The catheter is commonly incorporated into a catheter adapter to aid in the ease of use, accessibility, and utility of the catheter. A catheter adapter may be adapted to house one end of the catheter such that one end of the catheter is supported by the catheter adapter, and the body and tip of the catheter extends beyond a first end of the catheter adapter. A catheter adapter generally further includes a second end adapted to receive additional infusion components for use with the catheter. For example, the second end of a catheter adapter may include a set of threads for attaching an intravenous line or for coupling a syringe to the catheter adapter, thereby providing access to the patient's vasculature via the attached catheter.

The catheter may be inserted transcutaneously. When inserted transcutaneously, the insertion of the catheter is commonly aided by an introducer needle. The introducer needle is commonly housed inside the lumen of the catheter such that the gauge of the needle approximates the inner diameter of the catheter. The needle is positioned within the catheter such that the needle tip extends beyond the tip of the catheter whereby the needle is used to penetrate the patient's vein and provide an opening for insertion of the catheter.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal, fluid infusion, or probe access.

Blood withdrawal or infusion using the catheter may be difficult for several reasons, particularly when a dwelling time of the catheter within the patient is more than one day.

For example, when the catheter is left inserted in the patient for a prolonged period of time, the vein and catheter may be more susceptible to narrowing, collapse, kinking, blockage by debris (e.g., fibrin, platelet clots, or thrombus), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is desired, an additional needle stick is used to provide vein access for blood collection, which may be painful for the patient and result in higher material costs.

SUMMARY OF THE INVENTION

In one aspect or embodiment, a vascular access device includes an adapter body having a first end and a second end positioned opposite the first end, with the adapter body defining a passageway, a catheter received by the adapter body, a needle received by the adapter body with a portion of the needle positioned within the catheter, and a seal assembly including a seal body positioned within the passageway of the adapter body and an actuator. The seal body forms a seal with the adapter body and the catheter is connected to the seal body. The actuator is configured to move the seal body from a first position within the adapter body to a second position within the adapter body that is spaced from the first position.

The vascular access device may include an end cap positioned at the first end of the adapter body, with the end cap configured to engage the seal body to limit movement of the seal body. The catheter may be connected to the seal body via a wedge. A portion of the catheter may be positioned over the wedge, with the wedge connected to the seal body via an interference fit.

The actuator may be an extension member connected to the seal body and extending outside of the passageway of the adapter body. An actuator seal may be positioned within the passageway of the adapter body, with the extension member and the needle received by the actuator seal.

The actuator may be a handle having a first magnet and a second magnet connected to the seal body, with at least a portion of the handle positioned outside of the passageway of the adapter body, and with movement of the handle configured to move the seal body between the first position and the second position via interaction between the first magnet and the second magnet. The first magnet may be arcuate and the second magnet may be annular. The handle and the first magnet may be received within a slot defined by the adapter body.

The actuator may be a knob having a pinion gear and a rack connected to the seal body and engaged with the pinion gear, with rotation of the knob rotating the pinion gear and moving the seal body between the first position and the second position. The knob is positioned outside of the passageway of the adapter body, with the pinion gear and the rack received within the passageway of the adapter body. The actuator may include a seal bearing positioned between the knob and the pinion gear, with the seal bearing configured to seal an opening of the adapter body that receives the knob. The rack may be formed integrally with the seal body.

The seal body may include a plurality of seal rings. The adapter body may include a side port extending between the first and second ends of the adapter body, with the side port defining a side passageway in fluid communication with the passageway of the adapter body. The side port may extend from the adapter body at an angle of 25-75 degrees.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Figure 1:
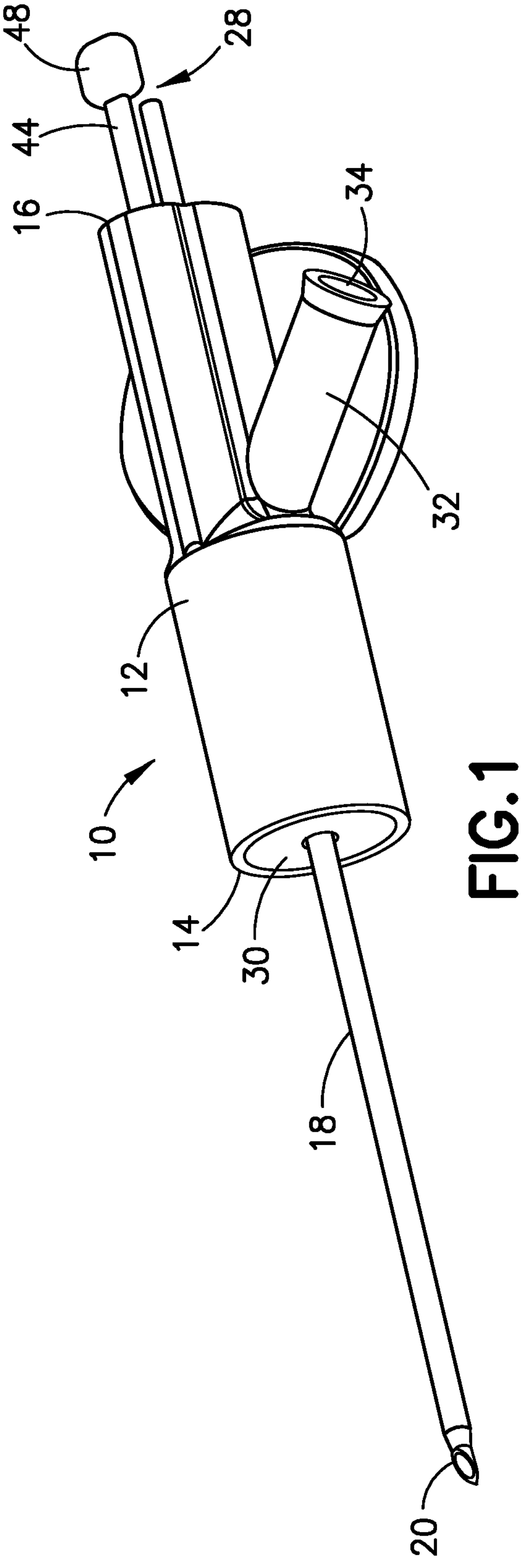
FIG. 1 is a perspective view of a vascular access device according to one aspect or embodiment of the present application.

Spatial or directional terms, such as “left”, “right”, “inner”, “outer”, “above”, “below”, and the like, are not to be considered as limiting as the invention can assume various alternative orientations.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention.

Unless otherwise indicated, all ranges or ratios disclosed herein are to be understood to encompass the beginning and ending values and any and all subranges or subratios subsumed therein. For example, a stated range or ratio of “1 to 10” should be considered to include any and all subranges or subratios between (and inclusive of) the minimum value of 1 and the maximum value of 10; that is, all subranges or subratios beginning with a minimum value of 1 or more and ending with a maximum value of 10 or less.

The terms “first”, “second”, and the like are not intended to refer to any particular order or chronology, but refer to different conditions, properties, or elements.

As used herein, “at least one of” is synonymous with “one or more of”. For example, the phrase “at least one of A, B, and C” means any one of A, B, or C, or any combination of any two or more of A, B, or C. For example, “at least one of A, B, and C” includes one or more of A alone; or one or more of B alone; or one or more of C alone; or one or more of A and one or more of B; or one or more of A and one or more of C; or one or more of B and one or more of C; or one or more of all of A, B, and C.

Referring to FIGS. 1-6, in one aspect or embodiment of the present application, a vascular access device 10 includes an adapter body 12 having a first end 14 and a second end 16 positioned opposite the first end 14, a catheter 18 received by the adapter body 12, a needle 20 received by the adapter body 12, and a seal assembly 22. The adapter body 12 defines a passageway 24 and a portion of the needle 20 is positioned within the catheter 18. The seal assembly 22 includes a seal body 26 positioned within the passageway 24 of the adapter body 12 and an actuator 28. The seal body 26 forms a seal with the adapter body 12. The catheter 18 is connected to the seal body 26. The actuator 28 is configured to move the seal body 26 from a first position within the adapter body 12 to a second position within the adapter body 12 that is spaced from the first position. As the catheter 18 is connected to the seal body 26, when the seal body 26 is moved between the first and second positions, the catheter 18 is extended and retracted relative to the adapter body 12.

Figure 2:
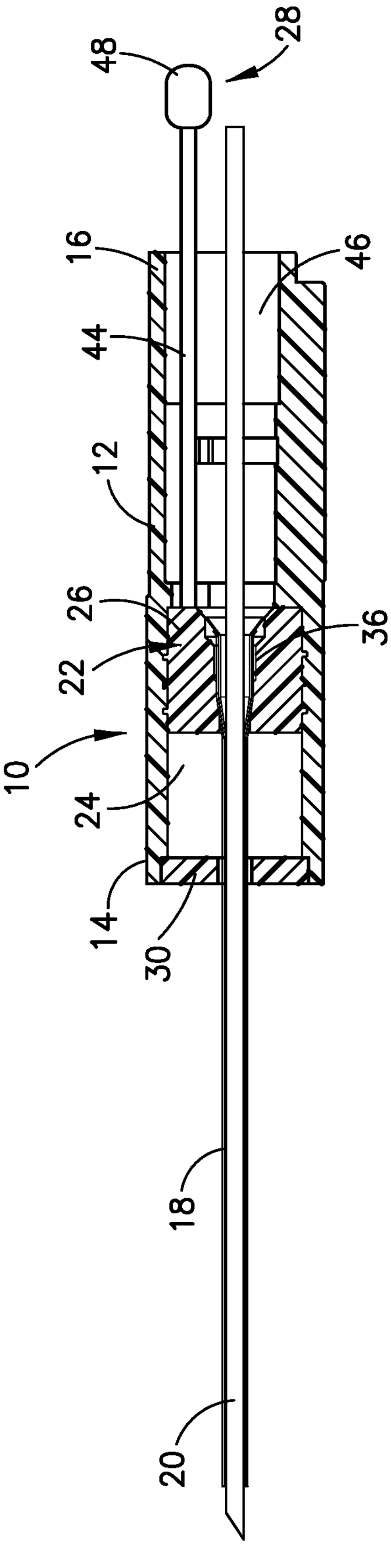
FIG. 2 is a cross-sectional view of the vascular access device of FIG. 1.
Figure 3:
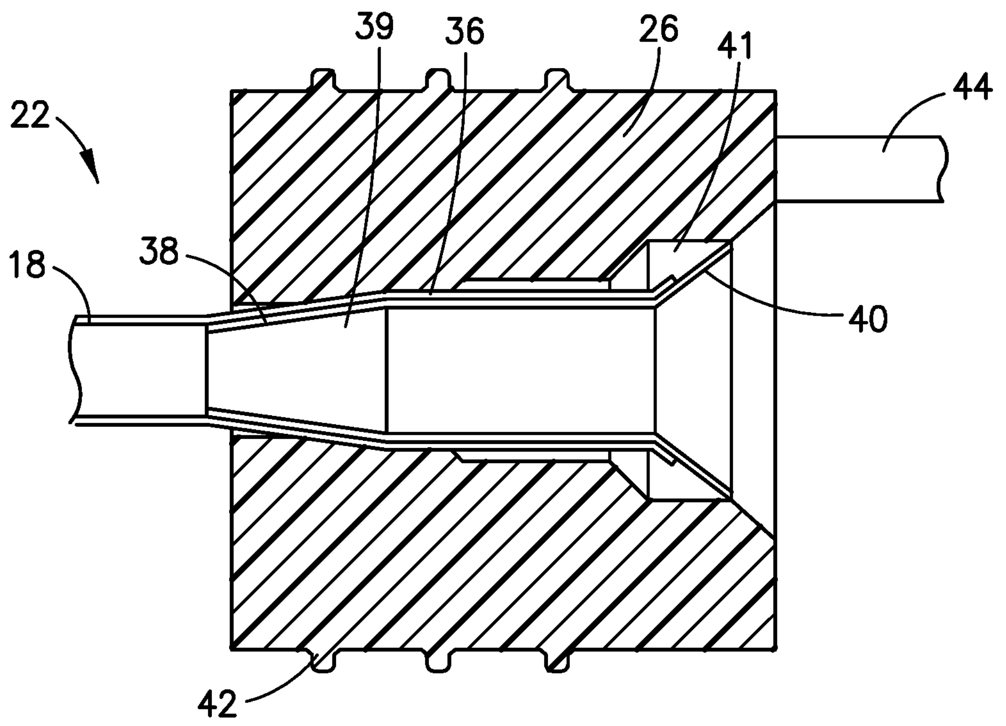
FIG. 3 is a partial cross-sectional view of the vascular access device of FIG. 1.
Figure 4:
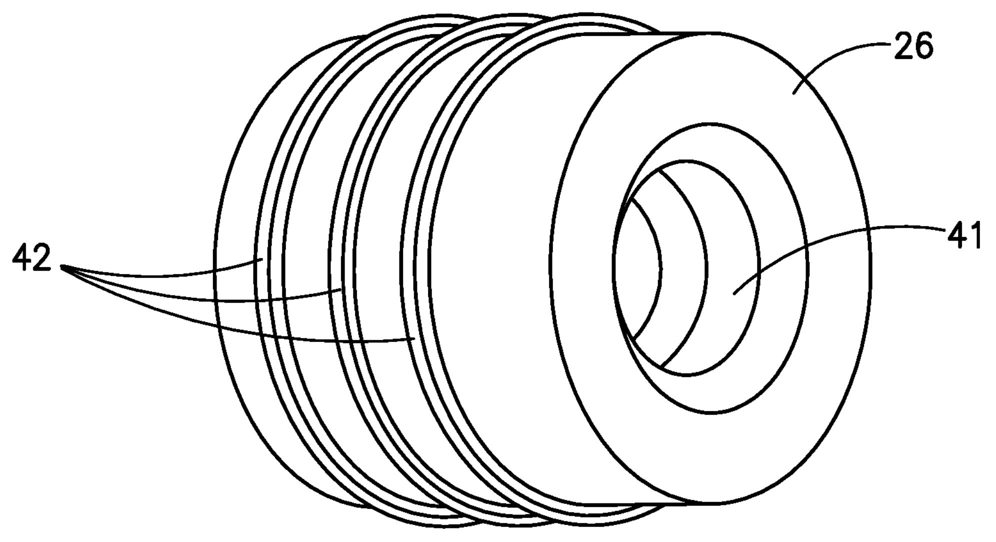
FIG. 4 is a perspective view of a seal assembly of the vascular access device of FIG. 1.

Referring to FIGS. 1 and 2, an end cap 30 is positioned at the first end 14 of the adapter body 12, with the end cap 30 configured to engage the seal body 26 to limit movement of the seal body 26. The end cap 30 may be formed integrally with the adapter body 12 or may be formed separately from the adapter body 12 and subsequently attached to the adapter body 12. The adapter body 12 includes a side port 32 extending between the first and second ends 14, 16 of the adapter body 12, with the side port 32 defining a side passageway 34 in fluid communication with the passageway 24 of the adapter body 12. The side port 32 extends from the adapter body 12 at an angle of 25-75 degrees, although other suitable angles may be utilized.

Referring to FIGS. 2, 3, 5, and 6, the catheter 18 is connected to the seal body 26 via a wedge 36, although other suitable arrangements may be utilized. A portion of the catheter 18 is positioned over the wedge 36, with the wedge 36 connected to the seal body 26 via an interference fit. The wedge 36 may be pressed or bonded to the seal body 26. The wedge 36 defines a central passageway 39 in line with the catheter 18. The wedge 36 has a tapered portion 38 configured to receive the catheter 18 and a flared portion 40, with the flared portion 40 having a larger diameter than the tapered portion 38. The seal body 26 defines a passageway 41 that receives the catheter 18 and the wedge 36. The passageway 41 of the seal body 26 may taper and/or include sections of decreased diameter to facilitate the interference fit with the wedge 36. The seal body 26 includes a plurality of seal rings 42 that form the seal with the adapter body 12. In one aspect or embodiment, the seal body 26 is formed from a polymer and the seal rings 42 are formed from an elastomer or silicone.

Figure 5:
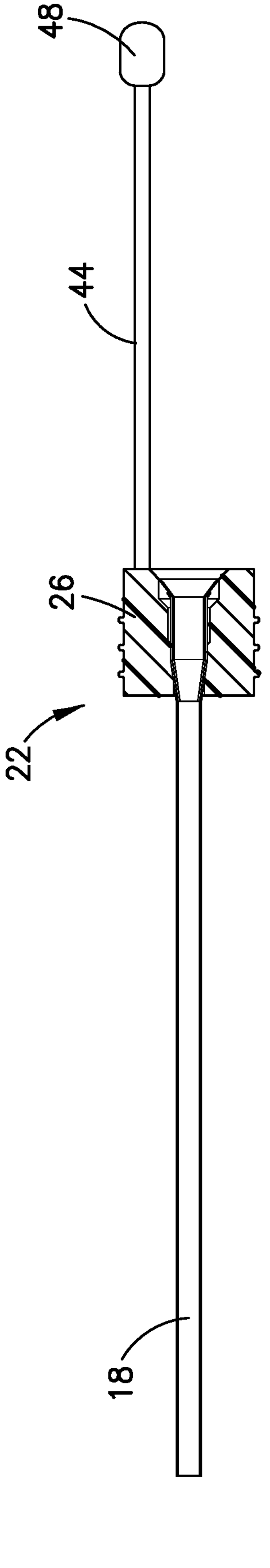
FIG. 5 is a cross-sectional view of a seal assembly and actuator member of the vascular access device of FIG. 1.
Figure 6:
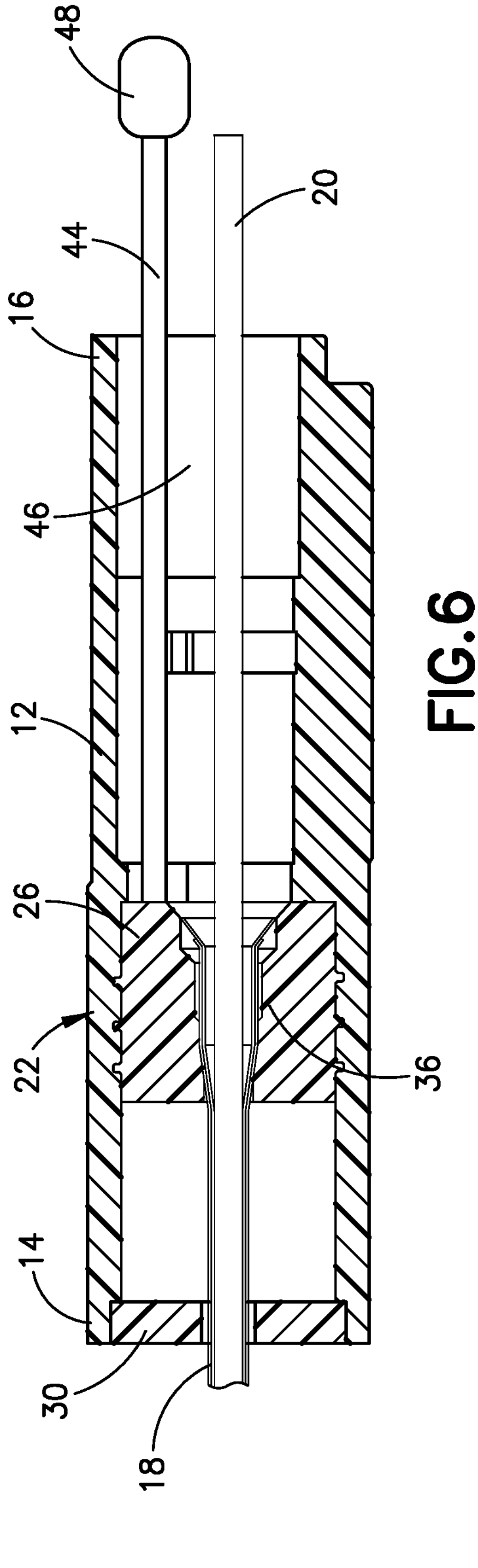
FIG. 6 is a partial cross-sectional view of the vascular access device of FIG. 1.
Figure 7:
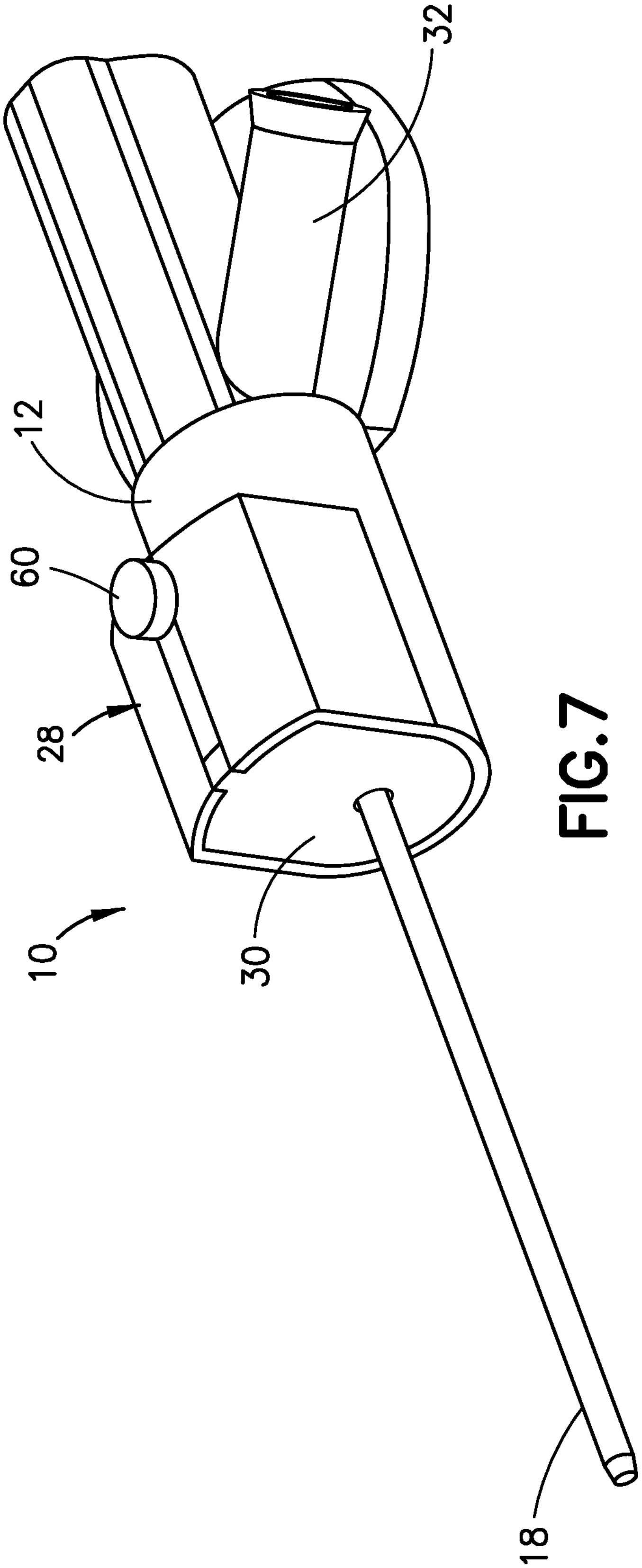
FIG. 7 is a perspective view of a vascular access device according to a further aspect or embodiment of the present application.
Figure 8:
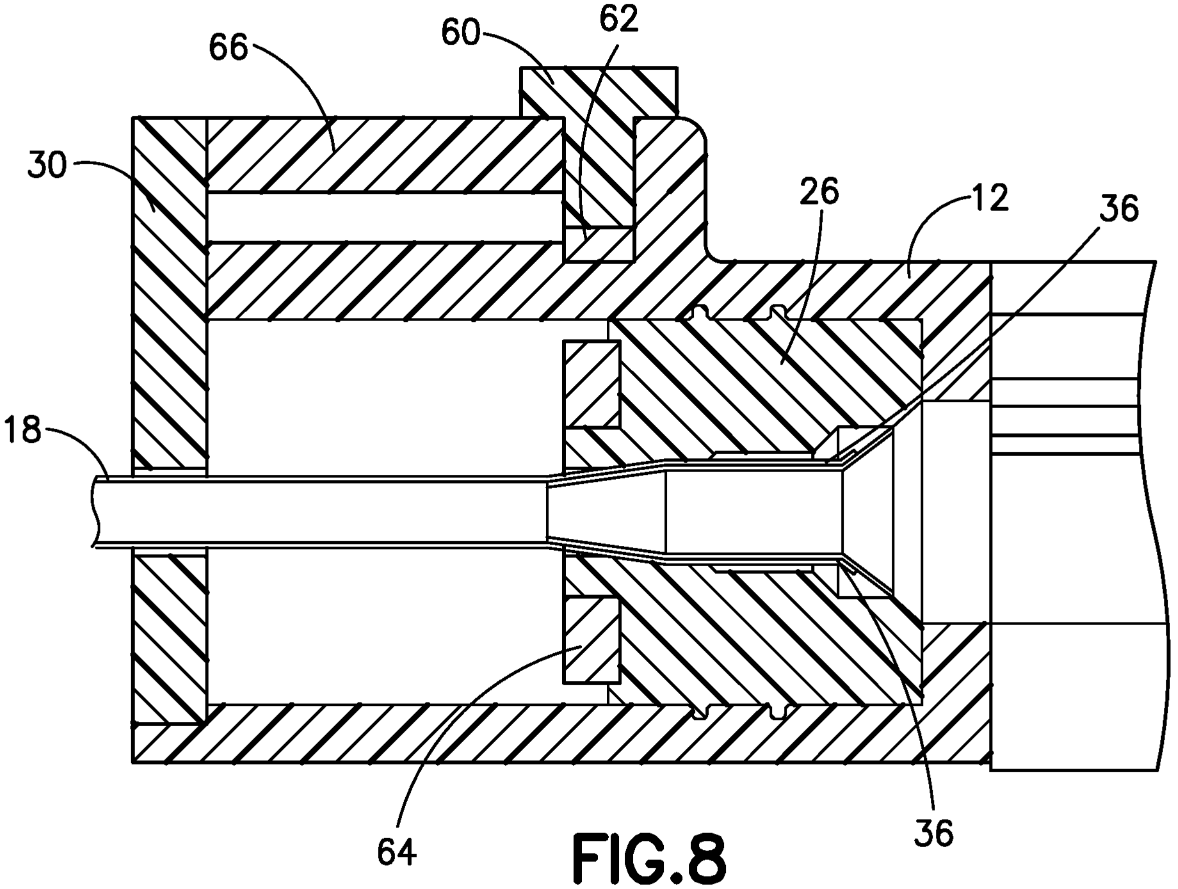
FIG. 8 is a partial cross-sectional view of the vascular access device of FIG. 7.
Figure 9:
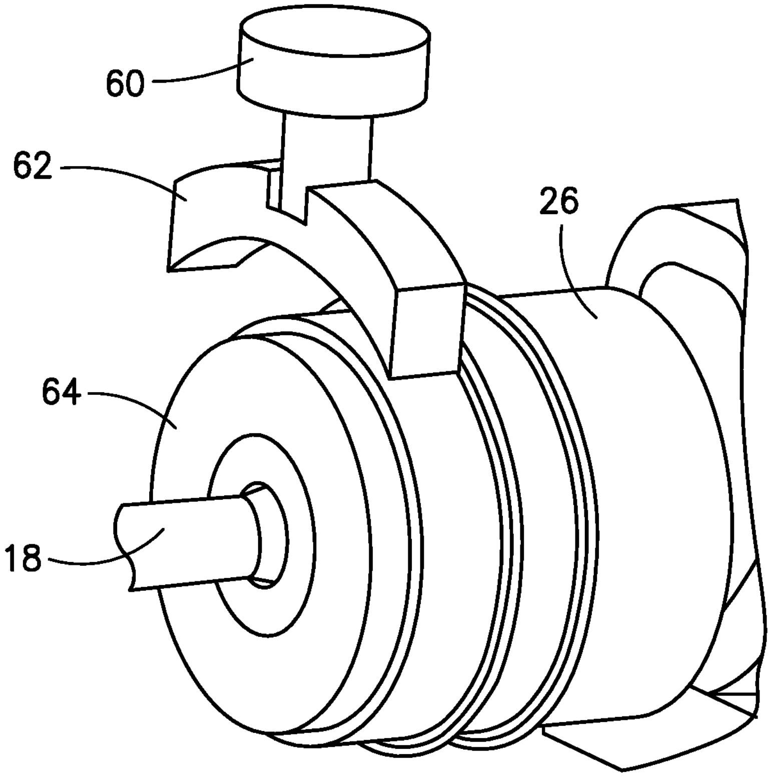
FIG. 9 is a partial perspective view of a seal assembly and actuator member of the vascular access device of FIG. 7.
Figure 10:
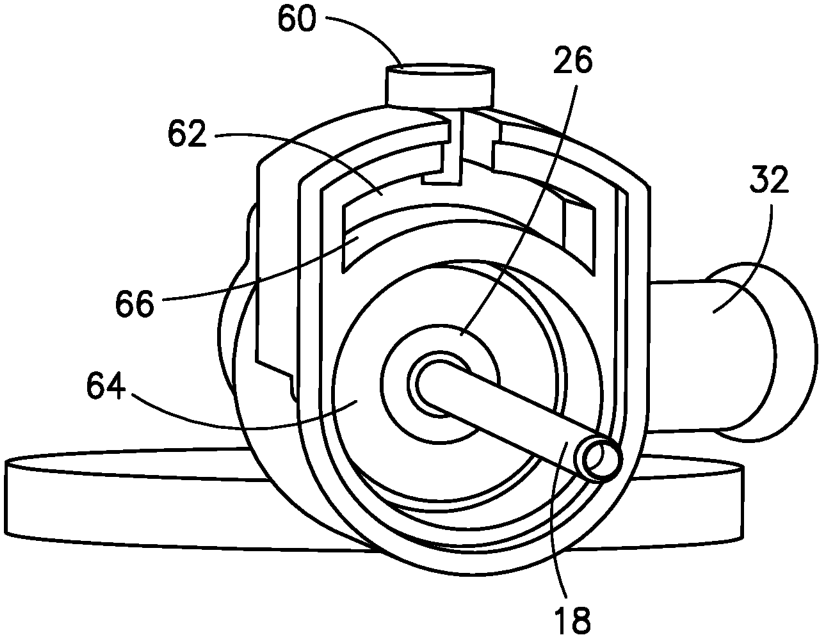
FIG. 10 is a front perspective view of a seal assembly and actuator member of the vascular access device of FIG. 7.
Figure 11:
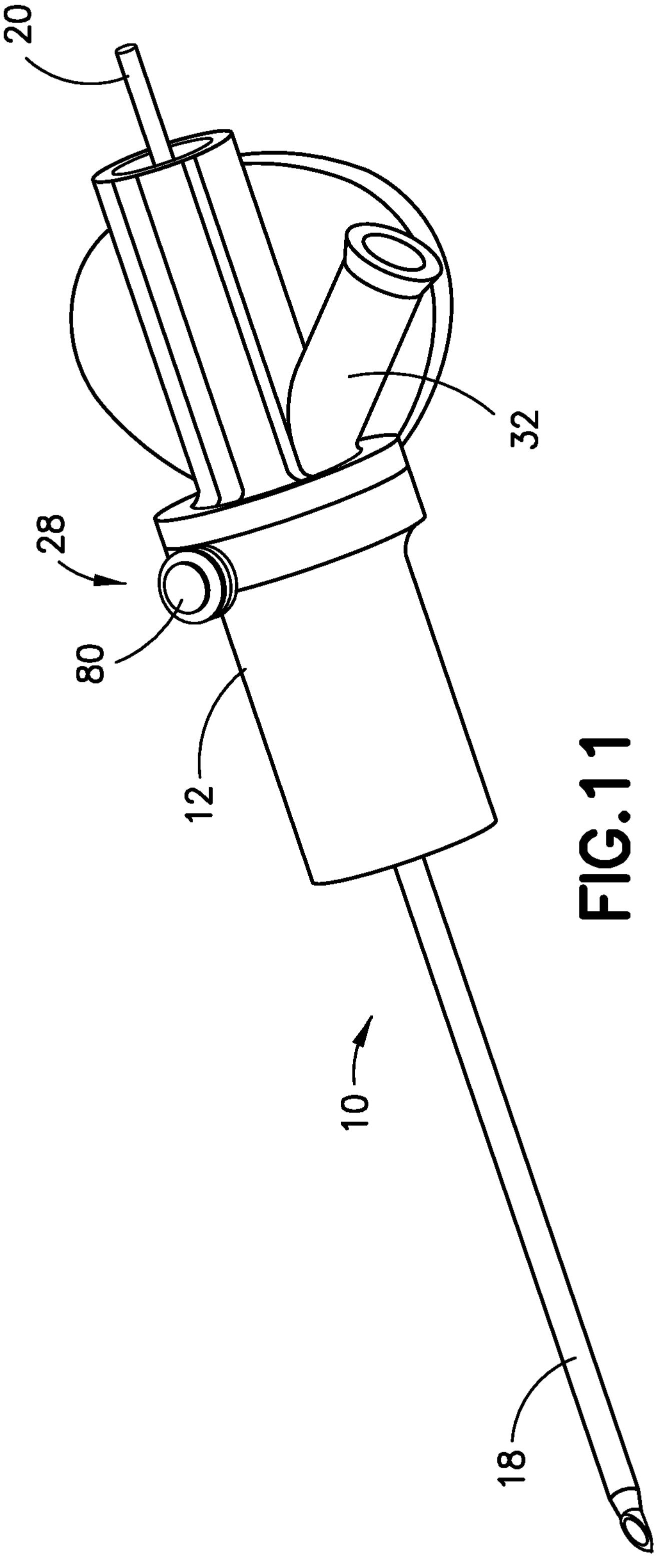
FIG. 11 is a perspective view of a vascular access device according to a further aspect or embodiment of the present application.
Figure 12:
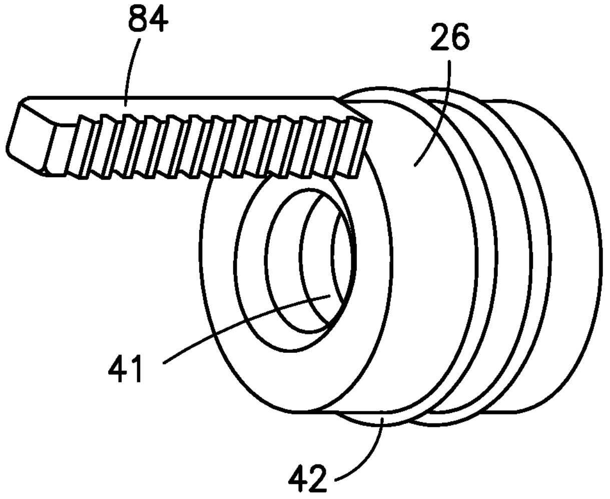
FIG. 12 is a perspective view of a seal assembly of the vascular access device of FIG. 11.
Figure 13:
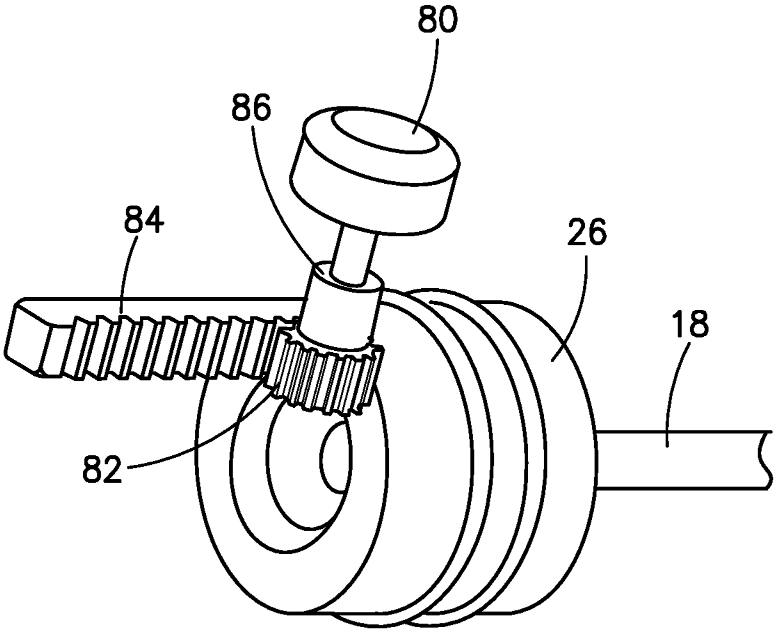
FIG. 13 is a perspective view of a seal assembly and actuator member of the vascular access device of FIG. 11.
Figure 14:
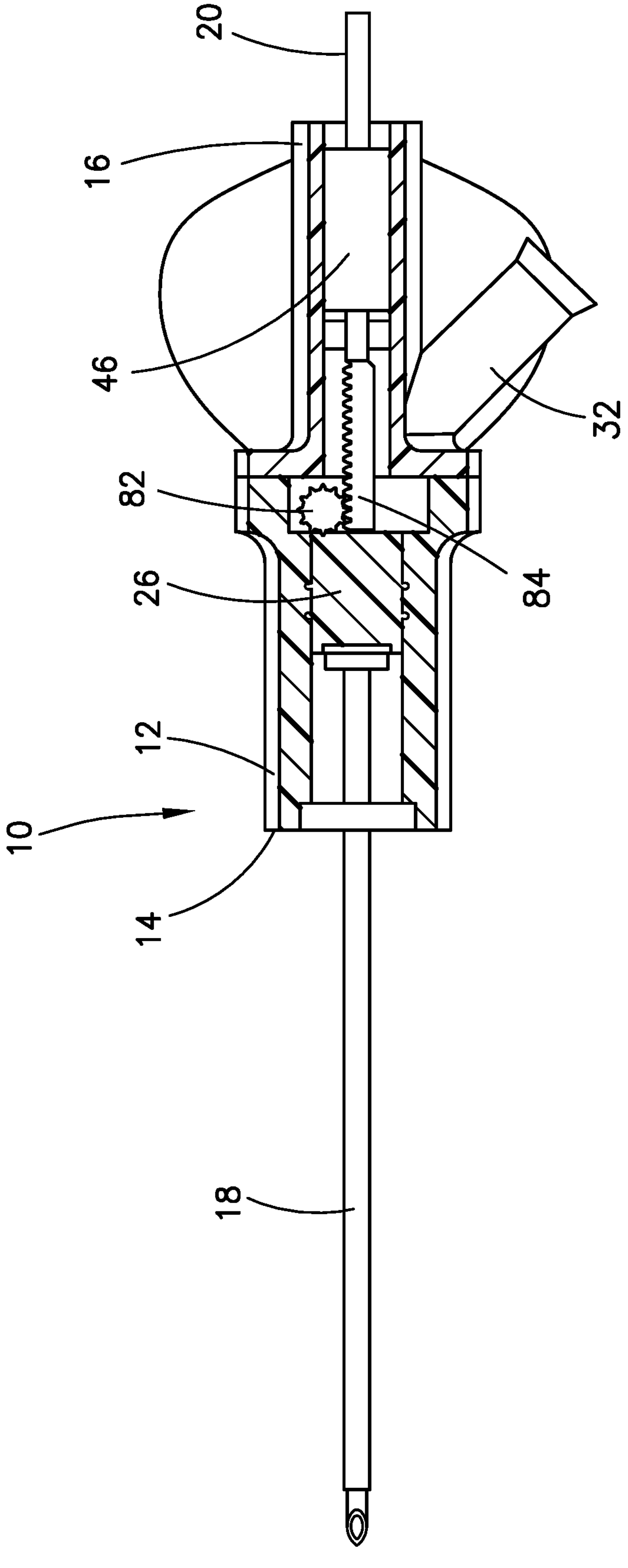
FIG. 14 is a top cross-sectional view of the vascular access device of FIG. 11.
Figure 16:
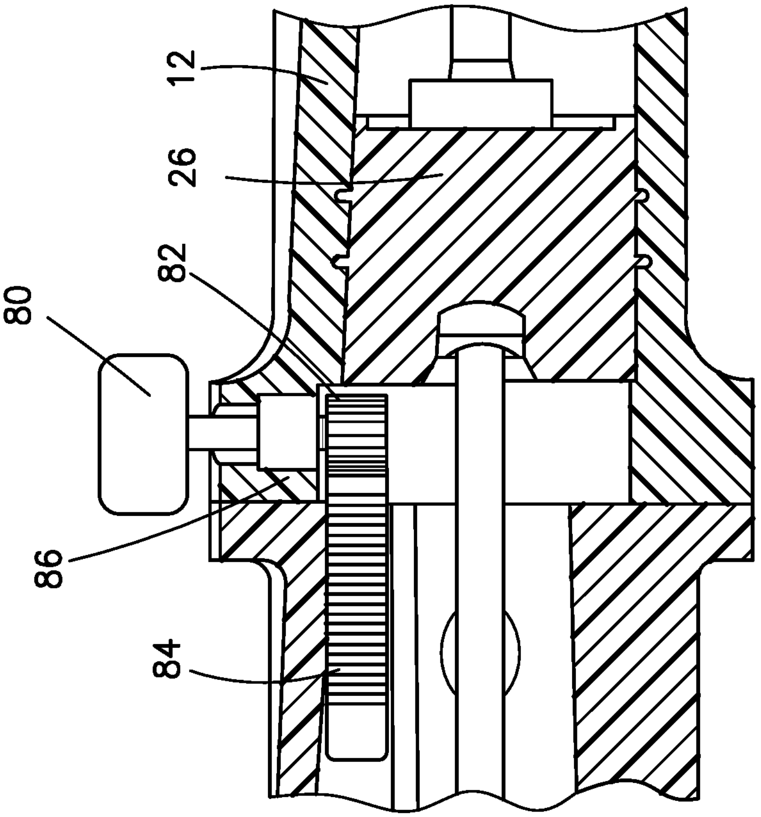
FIG. 16 is a partial cross-sectional view of the vascular access device of FIG. 11.
Figure 15:
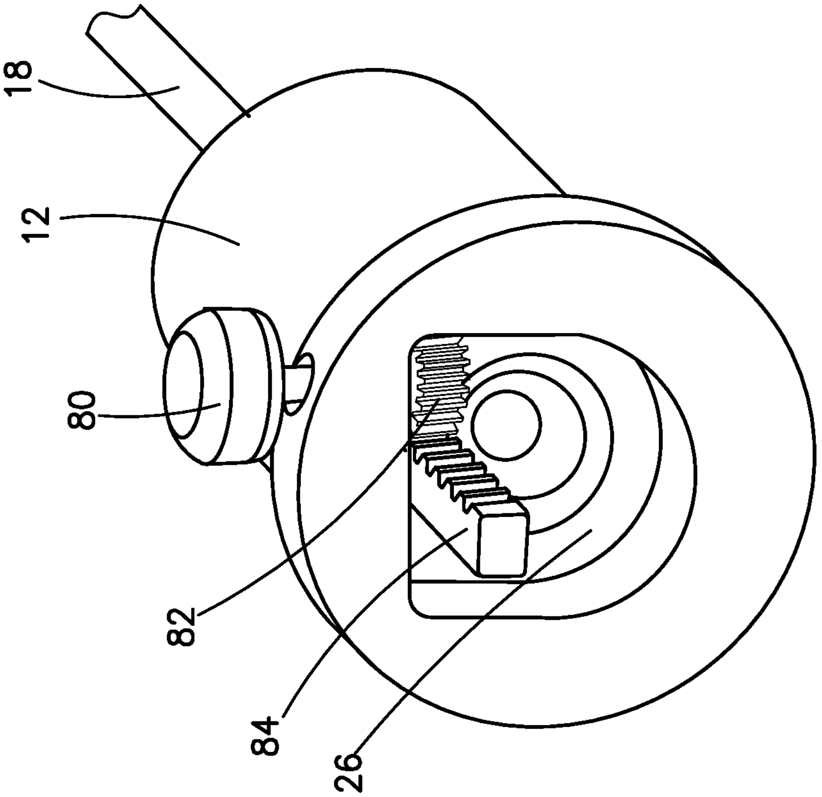
FIG. 15 is a partial front view of the vascular access device of FIG. 11.
Figure 17:
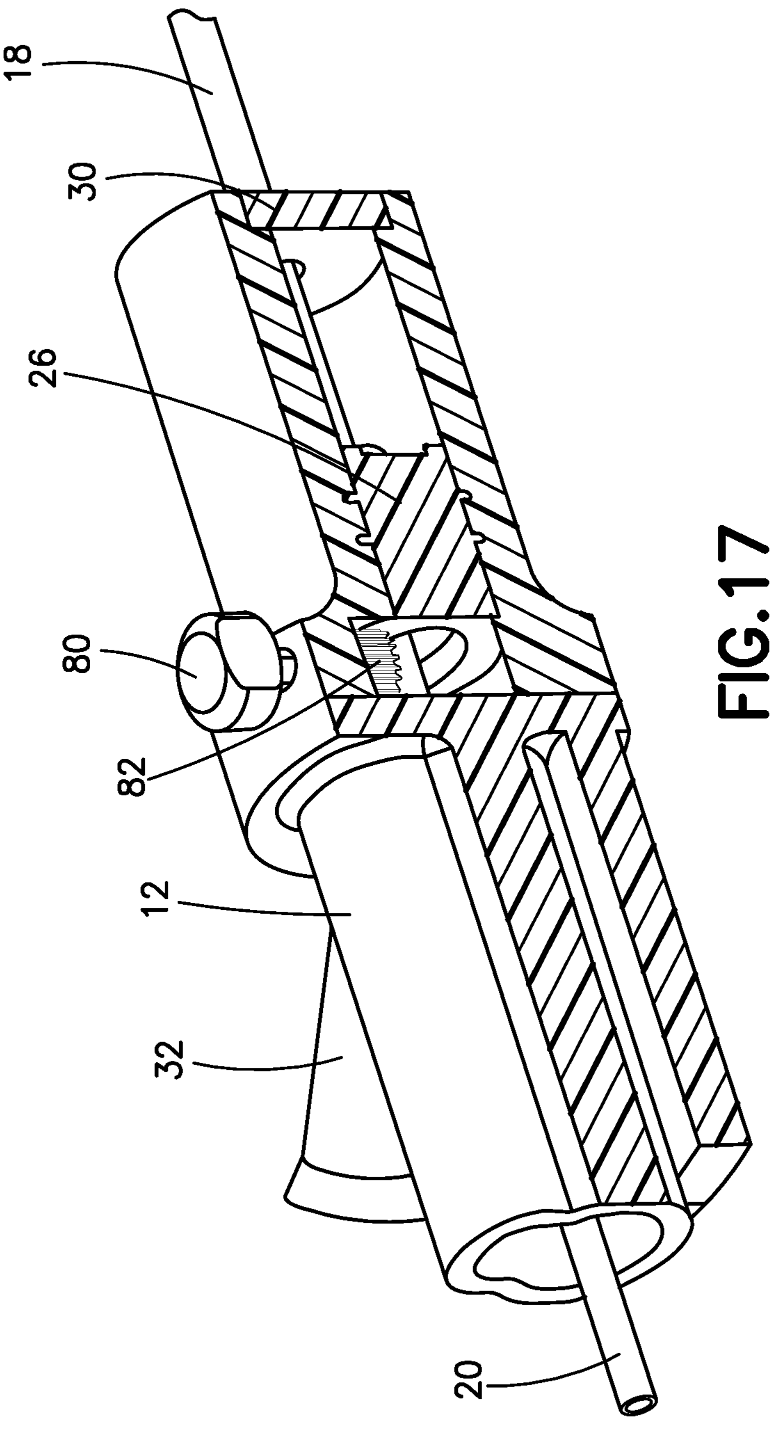
FIG. 17 is a partial cutaway view of the vascular access device of FIG. 11.

Referring to FIGS. 5 and 6, in one aspect or embodiment, the actuator 28 is an extension member 44 connected to the seal body 26 and extending outside of the passageway 24 of the adapter body 12. The extension member 44 may be formed integrally with the seal body 26 or may be formed separately and subsequently secured to the seal body 26. An actuator seal 46 is positioned within the passageway 24 of the adapter body 12, with the extension member 44 and the needle 20 received by the actuator seal 46. The actuator seal 46 is positioned at the second end 16 of the actuator body 12, although other suitable arrangements may be utilized. A length of the actuator seal 46 is configured to prevent the catheter 18 from being in fluid communication with any portion of the actuator 28 capable of being positioned outside of the passageway 24 of the adapter body 12. The extension member 44 includes a handle 48, although other suitable arrangements may be utilized.

Referring to FIGS. 7-10, in a further aspect or embodiment, the actuator 28 is a handle 60 having a first magnet 62 and a second magnet 64 connected to the seal body 26, with at least a portion of the handle 60 positioned outside of the passageway 24 of the adapter body 12. The movement of the handle 60 is configured to move the seal body 26 between the first position and the second position via interaction between the first magnet 62 and the second magnet 64. In one aspect or embodiment, the first and second magnets 62, 64 are rare earth magnets. In one aspect or embodiment, the first magnet 62 is attracted to the second magnet 64. The first magnet 62 is arcuate and the second magnet 64 is annular, although other suitable shapes and configurations may be utilized. The handle 60 and the first magnet 62 are received within a slot 66 defined by the adapter body 12. The slot 66 may be generally T-shaped, with a portion of the slot 66 conforming to the arcuate shape of the first magnet 62.

Referring to FIGS. 11-17, in a further aspect or embodiment, the actuator 28 is a knob 80 having a pinion gear 82 and a rack 84 connected to the seal body 26 and engaged with the pinion gear 82. Rotation of the knob 80 rotates the pinion gear 82 and moves the seal body 26 between the first position and the second position. The knob 80 is positioned outside of the passageway 24 of the adapter body 12, and the pinion gear 82 and the rack 84 are received within the passageway 24 of the adapter body 12. A seal bearing 86 is positioned between the knob 80 and the pinion gear 82, with the seal bearing 86 configured to seal an opening of the adapter body 12 that receives the knob 80. The rack 84 may be formed integrally with the seal body 26 or may be formed separately and subsequently attached to the seal body 26. The rack 84 extends in a direction extending from the first end 14 to the second end 16 of the adapter body 12.

The vascular access device 10 is configured to be inserted into a patient's vasculature like a shorter catheter, but allows for the catheter 18 to be extended by moving the seal body 26 from the first position to the second position for a blood draw and subsequently returned to the first position. Extending the catheter 18 allows for improved blood collection as well as decreased thrombus formation around the distal end of the catheter 18 with the distal end located further away from the insertion site. Extending the catheter 18 also reduces the risk of infiltration and extravasation due to the additional length of the catheter 18 inside the vein. Both of these advantages decrease occurrences of such adverse events leading to increased patient comfort and the possibility of extended dwell times. The vascular access device 10 may be inserted by nursing personnel without the use of ultrasound-guided insertion or specialty insertion teams. Many hospitals require the use of ultrasound-guided PIVC insertions in catheter lengths greater than 1.25 inch. However, the vascular access device 10 may be inserted into a patient's vasculature with typical insertion methods, not requiring ultrasound-guided insertion or specialty insertion teams.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A vascular access device comprising:

an adapter body having a first end and a second end positioned opposite the first end, the adapter body defining a passageway;

a catheter received by the adapter body;

a needle received by the adapter body, a portion of the needle positioned within the catheter; and a seal assembly comprising a seal body positioned within the passageway of the adapter body and an actuator, the seal body forming a seal with the adapter body, the catheter connected to the seal body, wherein the actuator is configured to move the seal body from a first position within the adapter body to a second position within the adapter body that is spaced from the first position, wherein the adapter body comprises a side port provided between the first and second ends of the adapter body, the side port defining a side passageway in fluid communication with a portion of the passageway of the adapter body, the fluid communication being maintained throughout movement of the seal body between the first position and the second position.

2. The vascular access device of claim 1, further comprising an end cap positioned at the first end of the adapter body, the end cap configured to engage the seal body to limit movement of the seal body.

3. The vascular access device of claim 1, wherein the catheter is connected to the seal body via a wedge.

4. The vascular access device of claim 3, wherein a portion of the catheter is positioned over the wedge, with the wedge connected to the seal body via an interference fit.

5. The vascular access device of claim 1, wherein the actuator comprises an extension member connected to the seal body and extending outside of the passageway of the adapter body.

6. The vascular access device of claim 5, further comprising an actuator seal positioned within the passageway of the adapter body, the extension member and the needle received by the actuator seal.

7. The vascular access device of claim 1, wherein the actuator comprises a handle having a first magnet and a second magnet connected to the seal body, at least a portion of the handle is positioned outside of the passageway of the adapter body, and wherein the movement of the handle is configured to move the seal body between the first position and the second position via interaction between the first magnet and the second magnet.

8. The vascular access device of claim 7, wherein the first magnet is arcuate, and wherein the second magnet is annular.

9. The vascular access device of claim 7, wherein the handle and the first magnet are received within a slot defined by the adapter body.

10. The vascular access device of claim 1, wherein the actuator comprises a knob having a pinion gear and a rack connected to the seal body and engaged with the pinion gear, wherein rotation of the knob rotates the pinion gear and moves the seal body between the first position and the second position.

11. The vascular access device of claim 10, wherein the knob is positioned outside of the passageway of the adapter body, and wherein the pinion gear and the rack are received within the passageway of the adapter body.

12. The vascular access device of claim 10, wherein the actuator comprises a seal bearing positioned between the knob and the pinion gear, the seal bearing configured to seal an opening of the adapter body that receives the knob.

13. The vascular access device of claim 10, wherein the rack is formed integrally with the seal body.

14. The vascular access device of claim 1, wherein the seal body comprises a plurality of seal rings.

15. The vascular access device of claim 1, wherein the side port extends from the adapter body at an angle of 25-75 degrees.

* * * * *